United States Patent [19]
Vigelius et al.

[11] 3,983,089
[45] Sept. 28, 1976

[54] NOVEL 1-ARYL-2-ARYLALKYL-3-OR-4-[4'-(SUBSTITUTED-ALKYL)-PIPERAZINO-1']-BUTANOLS-2 OR-BUTENES-1, AND METHODS OF MANUFACTURE THEREOF

[75] Inventors: Wolf-Dieter Vigelius, Denzlingen; Spyridon Marinis, Emmendingen, both of Germany

[73] Assignee: Warner-Lambert Company, Morris Plains, N.J.

[22] Filed: Aug. 25, 1975

[21] Appl. No.: 607,846

Related U.S. Application Data

[62] Division of Ser. No. 398,513, Sept. 18, 1973, Pat. No. 3,947,411.

[30] Foreign Application Priority Data

Sept. 21, 1972    Germany............................ 2246279

[52] U.S. Cl.......................... 260/240 K; 260/268 R
[51] Int. Cl.$^2$...................................... C07D 403/06
[58] Field of Search..................... 260/240 K, 268 R

[56] References Cited

UNITED STATES PATENTS 3,947,411    3/1976    Vigelius et al................. 260/240 R

FOREIGN PATENTS OR APPLICATIONS 2,246,279    5/1974    Germany........................ 260/268 K

OTHER PUBLICATIONS

Chemical Abstracts vol. 81, abst. No. 63680Q (1974) (abst. of German Offen. 2,246,279).
Chemical Abstracts Chem. Substance Index vol. 81, p. 261CS (1974).

Primary Examiner—John D. Randolph
Attorney, Agent, or Firm—Albert H. Graddis; Frank S. Chow; George M. Yahwak

[57] ABSTRACT

The present invention relates to novel 1-(aryl)-2-(arylalkyl)-3-(or-4-)-[4'-(substituted alkyl-)-piperazino-1']-butanols-2, and butenes-1 showing antimicrobial action, to their pharmaceutically acceptable salts, and to the process of manufacture thereof.

3 Claims, No Drawings

NOVEL 1-ARYL-2-ARYLALKYL-3-OR-4-[4'-(SUBSTITUTED-ALKYL)-PIPERAZINO-1']-BUTANOLS-2 OR-BUTENES-1, AND METHODS OF MANUFACTURE THEREOF

This is a division of application Ser. No. 398,513 filed Sept. 18, 1973, now U.S. Pat. No. 3,947,411 granted Mar. 30, 1976.

Recent developements in epidemiology and histopathologic techniques and the introduction of the polyene antibiotic amphotericin B as an effective antimycotic drug have led to an increased awareness of the medical problem of systemic fungal disease. The fact that infection occurs with fungi that are free-living forms in soil, decaying vegetation and bird excreta provides a safe speculation that systematic mycoses will continue to be an increasing cause of human disease.

Among the most prevalent of the mycotic diseases are the diseases aspergillosis and candidosis.

Aspergillosis is world-wide in distribution and appears as an infection of the lung, from where it may disseminate to bone, meninges, heart, or other organs. The genus Aspergillus is the pathogen which produces this invasive disease, and although all species within the genes are potentially pathogenic, the organism A. fumigatus is the most common pathogen.

Candidosis, or thrush, is an acute or chronic fungal disease involving the superficial tissues of skin or mucous membrane or less frequently producing systemic disease, especially in kidneys, heart, and brain. Thrush was first described by Underwood in 1784; the organism c. albicans was discovered in 1839 by von Langenbeck, and that this organism was the cause of thrush was demonstrated two years later by Berg.

It has now been found that novel 1-aryl-2-arylalkyl-3-or-4-[4'-(substituted alkyl)-piperazino-1']-butanols-2or butenes-2 of the general formula:

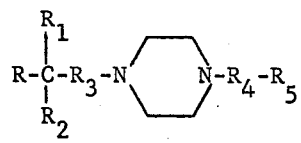

wherein R is a radical selected from the group consisting of:

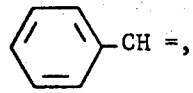

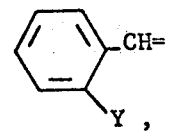

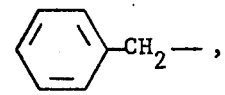

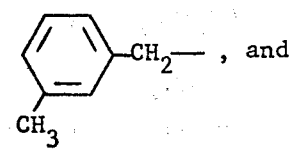

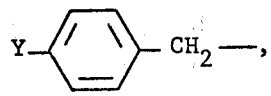

wherein Y is I, Cl, Br, or F; wherein $R_1$ is —OH, with the proviso that $R_1$ exists only when R is:

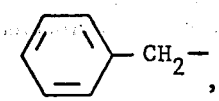

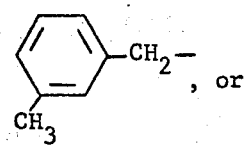

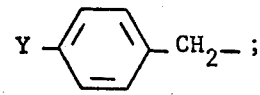

wherein $R_2$ is a radical selected from the group consisting of:

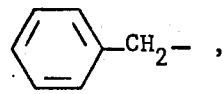

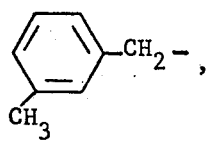

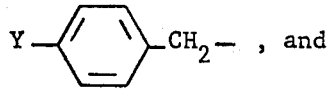

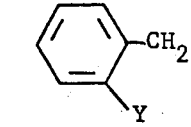

wherein Y has the meaning given above; wherein $R_3$ is a radical selected from the group consisting of:
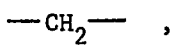
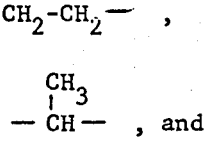
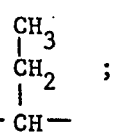
wherein $R_4$ is a radical selected from the group consisting of:
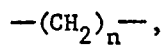
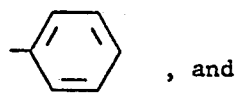
–H,
wherein $n$ is an interger from zero to eight; wherein $R_5$ is a radical selected from the group consisting of:
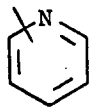
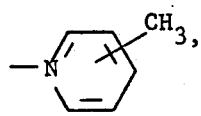
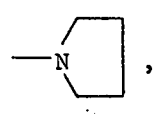
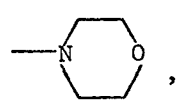
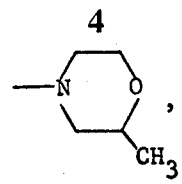
–OH,
–Y,
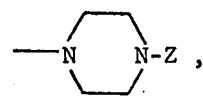
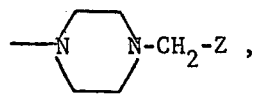
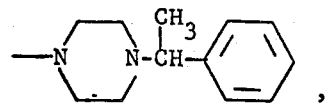
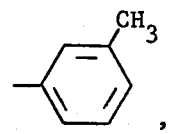
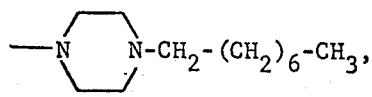
–NH-CH$_2$-(CH$_2$)$_6$-CH$_3$,
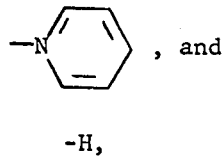
–H, wherein Y has the meaning given above, and wherein Z is selected from the group consisting of:

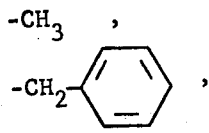

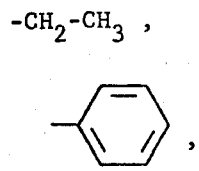

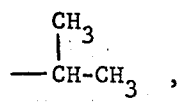

—H, and combinations thereof; show antimicrobial activity against among others the organisms implicated in these two diseases.

Accordingly, it is the object of this invention to disclose a series of novel compounds, and methods for their production, which show antimicrobial action, especially against Aspergillus and Candida.

For the base compound from which the specific compounds of this invention are manufactured, the methods described below may be used:

| | |
|---|---|
| 1) 1-phenyl-2-benzyl-3-[4'-basically substituted alkyl-piperazino-1']-butanols-2 | A – D |
| 2) 1-phenyl-2-benzyl-3-[4'-basically substituted alkyl-piperazino-1']-butenes-1 | E – F |
| 3) 1-phenyl-2-benzyl-3-[4'-alkyl substituted piperazino-1']-butanols-2 | G |
| 4) α,α'-diphenyl-α''-alkyl-α''-(4-alkyl-piperazino-1)-t-butanols | I |
| 5) 1-phenyl-2-benzyl-4-[4'-(alkylic-basically substituted-alkyl)-piperazino-1']-butanols-2 | H |

METHOD A

I. Benzyl piperazine is reacted in a solvent, (such as an alcohol, ether or benzene) preferably ethanol, with an equimolar quantity of an ester of an α-halogeno-propionic acid, preferably the methyl or ethyl ester of α-bromopropionic acid, in the presence of an inorganic or organic hydrohalide captor, preferably potassium carbonate, at temperatures between 20° and 120°C, preferably at the boiling point of the respective solvent; freed of inorganic salts by filtration; the filtrate is evaporated and the residue dissolved in diluted acid aqueous solution such as diluted hydrochloric acid; freed from non-reacted halogeno-propionic acid ester by extraction, e.g. with diethylether; made alkaline and the resulting free base extracted with diethylether, evaporated and purified by distillation.

II. The α-(-4-benzyl piperazino)-propionic acid ester obtained is reacted with the corresponding benzyl magnesium halide in diethylether under conditions which are usual for Grignard reactions and the obtained base is transformed into a suitable salt (e.g. the hydrochloride) for purification.

III. The salt of the correspondingly substituted 1-phenyl-2-benzyl-3-(4'-benzylpiperazino-1')-butanol-2 so obtained is debenzylized with hydrogen in a suitable solvent mixture, e.g. 50% methanol, and with a suitable catalyst such as palladium animal charcoal.

IV. The salt of the respectively substituted 1-phenyl-2-benzyl-3-piperazino-butanol-2 obtained is transformed into the free base and metallized under nitrogen in dry toluene or other suitable solvent with the aid of a suitable organometallic compound, such as phenyl lithium, and reacted with the corresponding aminoalkyl halide. (Refluxing for several hours while stirring has a favorable influence on the reaction).

METHOD B

I. Piperazine (anhydrous or hexahydrate) is reacted in a suitable solvent, preferably ethanol, with one half of the stoichiometric quantity of the respective alkyl halogenohydrine at temperatures between 20° and 120°C preferably at the boiling point of the solvent, for 1 to 20 hours. The solvent is evaporated and the reaction product purified by vacuum distillation.

II. The piperazino-alkanol obtained is reacted in a suitable solvent, such as ethanol, with an equimolar quantity of an α-halogeno-propionic acid ester, preferably α-bromopropionic acid ethyl ester, with stirring and boiling for 2 to 20 hours. After evaporation of the solvent, the crude possibly viscous oily hydrohalide is collected.

III. The crude hydrohalide of the α-[4-(hydroxyalkyl)-piperazine-1]-propionic acid ester obtained is refluxed, with stirring, in a suitable solvent, such as chloroform, with a suitable halogenation agent, preferably thionylchloride, for 1 to 10 hours and purified by crystallization after evaporation of the solvent.

IV. The base set free from the α-[4-(halogeno-alkyl)-piperazino-1]-propionic acid ester hydrohalide obtained is, as described in Method A II, transformed into the respective 1-phenyl-2-benzyl-3-[4'-(halogenoalkyl)-piperazino-1']-butanol-2-hydrohalide.

V. The salt obtained is refluxed in an excess of the respective amine for 2 to 20 hours or, in the case of an amine with low boiling point, heated in a suitable solvent such as ethanol, in an autoclave at a temperature between 60° and 130°C for the same time. After having removed the excessive starting amine and its salt by evaporation or filtration, the reaction product is transformed, in a suitable solvent, preferably diethylether, into a salt for purification.

METHOD C

I. The hydrohalide of the α-4-(halogeno-alkyl-piperazino-1) propionic acid ester, obtained according to Method B III is reacted as described in Method B V.

II The α-[4-(substituted-amino-alkyl)-piperazino-1]-propionic acid ester obtained is reacted to the respective 1-phenyl-2-benzyl-3-[4'-(substituted-aminoalkyl)-piperazino-1']-butanol, according to the Grignard reaction described in Method A II.

METHOD D

I. The piperazino-alkanol (described in Method B I) is transformed into its hydrohalide and converted into the corresponding halogeno-alkyl-piperazine salt according to Method B III.

II. The halogeno-alkyl-piperazine salt is reacted with the respective amine according to Method B V.

III. The substituted-amino-alkyl-piperazine obtained is processed further according to the Methods A I and A II, respectively.

METHOD E

I. The hydrohalide of the α-[4-(hydroxy-alkyl)-piperazino-1]-propionic acid ester obtained according to Method B II is transformed into the base and subjected to the Grignard reaction according to Method A II.

II. The hydrohalide of the 1-phenyl-2-benzyl-3-[4'-hydroxyalkyl)-piperazino-1']-butanol-2 obtained is refluxed in a halogenation agent, preferably thionylchloride, for 1 to 10 hours. The resultant product is cooled, filtered, and purified by crystallization.

III. The hydrohalide of the 1-phenyl-2-benzyl-3-[4'-(halogenoalkyl)-piperazino-1']-butene-1 obtained is reacted with the corresponding amine, according to Method B V, to the corresponding 1-phenyl-2-benzyl-3-[4'-(substituted-aminoalkyl)-piperazine-1']-butene-1.

METHOD F

The 1-phenyl-2-benzyl-3-[4'-(halogeno-alkyl)-piperazino-1'-butanol-2 hydrohalide, obtained according to Method B IV, is reacted according to Method E II and Method E III to 1-phenyl-2-benzyl-3-[4'-(substituted amino-alkyl)-piperazino-1']-butene-1.

METHOD G

The respective mono-substituted piperazine is reacted according to Method A I and Method A II, to the hydrohalide of 1-phenyl-2-benzyl-3(4'-alkyl-piperazino-1')-butanol.

METHOD H

I. The corresponding mono-substituted piperazine or the piperazine obtained according to Method B I or Method D II, is added to an equimolar quantity of acrylic acid ester, preferably the ethyl ester, at temperatures between −10° and +10°C, and allowed to stand at temperatures between 10° and 30°C for 3 to 8 days. The resulting reaction product is collected by vacuum distillation or by transformation of the product into a suitable salt. Products whose starting piperazines were produced according to Method B I can further be reacted into β-[4'-(halogeno-alkyl)-piperazino-1']-propionic acid esters according to Method B III.

II. The β-(4'-substituted-piperazino-1')-propionic acid ester obtained is reacted according to Method A II to the salt of the respective 1-phenyl-2-benzyl-4-(4'-substituted-piperazino-1')-butanol-2.

III. The 1-phenyl-2-benzyl-4-[4'-(halogeno-alkyl)-piperazino-1']-butanol-2 salt obtained is reacted to the corresponding 1-phenyl-2-benzyl-4[4'-(substituted-amino-alkyl)-piperazino-1']-butanol-2 according to Method B V.

METHOD I

I. The corresponding mono-substituted piperazine or the piperazine obtained according to the Methods B I or D II, is reacted according to Method A I with a correspondingly substituted α-halogeno acetic acid ester, such as α-bromo-acetic acid ethyl ester or α-bromo-butyric acid ethyl ester, to the corresponding 4-substituted-piperazino-1-acetic (or butyric) acid esters. Those products whose starting piperazines were produced according to Method B I, can further be reacted into β-[4'-(halogeno-alkyl)-piperazino-1']-acetic (or butyric) acid esters according to Method B III.

II. The esters obtained are further reacted as described in Method H II, into the salts of β,β'-diphenyl-β''-(4'-substituted-piperazino-1')-t-butanols or 1-phenyl-2-benzyl-3-(4'-substituted-piperazino-1')-4-methyl-butanols-2, respectively.

III. The salts thus obtained are reacted to the corresponding ββ'-diphenyl-β''-[4'-(substituted-amino-alkyl)-piperazino-1']-t-butanols, and 1-phenyl-2-benzyl-3-[4'-substituted-amino-alkyl)-piperazino-1']-4-methyl-butanol-2, respectively according to Method B V.

The physiologically harmless and pharmaceutically acceptable salts for the above bases are manufactured in the usual way by dissolving the respective base in ether and precipitating the salt either by introducing a gaseous dried acid such as hydrogen chloride, or by adding a dried solution of the acid in ether or in other suitable solvents. The quaternary salts are also produced in the usual way be dissolving the tertiary base in a suitable solvent, e.g. alcohol, and by adding the respective alkyl-halide, e.g. n-octylbromide. (Examples for the manufacture of the salts are included in the examples for the manufacture of the bases).

The following list contains examples of those compounds which are made according to the methods disclosed. (The individual compounds are identified by elementary analyses and infrared spectra, by ultra-violet or nuclear resonance spectra, if necessary.) Individual melting points and solubilities (in water) are also given as is the method by which each compound is prepared.

I 1-phenyl-2-benzyl-3-[4'-(β-dimethylamino-ethyl)-piperazino-1']-butanol-2; m.p. 263° − 264°C, sol. 10% (method C)

II 1-phenyl-2-benzyl-3-[4'-(β-diethylaminoethyl)-piperazino-1']-butanol-2; m.p. 225° − 227°C, sol. 5% (method A)

III 1-phenyl-2-benzyl-3-[4'-(β-pyrrolidino-ethyl)-piperazino-1']-butanol-2; m.p. 246° − 247°C, sol. 5% (method A)

IV 1-phenyl-2-benzyl-3-[4'-(β-piperidino-ethyl)-piperazino-1']-butanol-2; m.p. 240° − 242°C, sol. 5% (method A)

V 1-phenyl-2-benzyl-3-[4'-(β-morpholino-ethyl)-piperazino-1']-butanol-2; m.p. 245° − 247°C, sol. 5% (method D)

VI 1-phenyl-2-benzyl-3- 4'-[β-(2''-methyl-morpholino)-ethyl]-piperazino-1' -butanol-2; m.p. 242° − 243.5°C, sol. 10% (method A)

VII 1-phenyl-2-benzyl-3- 4'-[β-(2''-methyl-piperidino)-ethyl]-piperazino-1' -butanol-2; m.p. 234° − 236°C, sol. 5%, (method A)

VIII 1-phenyl-2-benzyl-3- 4'-[β-(3''-methyl-piperidino)-ethyl]-piperazino-1' butanol-2; m.p. 248° – 250°C, sol. 5%, (method A)

IX 1-phenyl-2-benzyl-3- 4'-[β-(4''-methyl-piperidino)-ethyl]-piperazino-1' -butanol-2; m.p. 255° – 256°C, sol. 5%, (method C)

X 1-phenyl-2-benzyl-3- 4'-[β-(4''-methyl-piperazino-1''')-ethyl]-piperazino-1' -butanol-2; m.p. 253° – 254°C, sol. 10%, (method C)

XI 1-phenyl-2-benzyl-3- 4'-[β-(4''-phenyl-piperazino-1''')-ethyl]-piperazino-1' -butanol-2; m.p. 257° – 257.5°C, sol. 5%, (method C)

XII 1-phenyl-2-benzyl-3- 4'-[β-(4''-benzyl-piperazino-1''')-ethyl]-piperazino-1' -butanol-2; m.p. 248° – 249°C, sol. 10%, (method C)

XIII 1-phenyl-2-benzyl-3- 4'-[β-(4''-α-phenethyl-piperazino-1''')-ethyl]-piperazino-1' -butanol-2; m.p. 261° – 262°C, sol. 10%, (method C)

XIV 1-phenyl-2-benzyl-3- 4'-[β-(4''-β-phenethyl-piperazino-1''')-ethyl]-piperazino-1' -butanol-2; m.p. 265° – 266°C, sol. 10%, (method C)

XV 1-phenyl-2-benzyl-3-[4'-(β-N-methyl-benzylaminoethyl)-piperazino-1']-butanol-2; m.p. 230° – 231°C, sol. 10%, (method C)

XVI 1-phenyl-2-benzyl-3-[4'-(β-dibenzylaminoethyl)-piperazino-1']-butanol-2; m.p. 207° – 207.5°C, sol. 5%, (method C)

XVII 1-phenyl-2-benzyl-3-[4'-(β-N-ethyl-N-benzylamino ethyl)-piperazino-1']-butanol-2; m.p. 85° – 90°C, sol. 10%, (method C)

XVIII 1-phenyl-2-benzyl-3-[4'-(β-N-phenyl-N-methyl-aminoethyl)-piperazino-1']-butanol-2; m.p. 218° – 219°C, sol. 1%, (method C)

XIX 1-phenyl-2-benzyl-3-[4'-(γ-piperidinopropyl)-piperazino-1']-butanol-2; m.p. 239° – 241°C, sol. 10%, (method A)

XX 1-phenyl-2-benzyl-3-[4'-(w-piperidino-n-hexyl)-piperazino-1']-butanol-2; m.p. 242°C, sol. 10%, (method B)

XXI 1-m-tolyl-2-m-methylbenzyl-3-[4'-(βpiperidino-ethyl)-piperazino-1']-butanol-2; m.p. 244° – 245°C, sol. 10%, (method D)

XXII 1-phenyl-2-benzyl-3-[4'-(2''-pyridylmethyl)-piperazino-1']-butanol-2; m.p. 222°C, sol. 5%, (method A)

XXIII 1-phenyl-2-benzyl-3-[4'-(3''-pyridylmethyl)-piperazino-1']-butanol-2; m.p. 235° – 236°C, sol. 5%, (method A)

XXIV 1-phenyl-2-benzyl-3-[4'-(4''-pyridylmethyl)-piperazino-1']-butanol-2; m.p. 205° – 207°C, sol. 10%, (method A)

XXV 1-phenyl-2-benzyl-3-[4'-(β-methylamino-ethyl)-piperazino-1']-butene-1; m.p. 222° – 223°C, sol. 10%, (method E)

XXVI 1-phenyl-2-benzyl-3-[4'-(β-dimethylamino-ethyl)-piperazino-1']-butene-1; m.p. 236° – 237°C, sol. 10%, (method E)

XXVII 1-phenyl-2-benzyl-3-[4'-(β-dimethylamino-ethyl)-piperazino-1']-butene-1; m.p. 187° – 188°C, sol. 10%, (method E)

XXVIII 1-phenyl-2-benzyl-3-[4'-(β-diisopropylamino-ethyl)-piperazino-1']-butene-1; m.p. 140° – 141°C, sol. 1%, (method E)

XXIX 1-phenyl-2-benzyl-3-[4'-(β-pyrrolidino-ethyl)-piperazino-1']-butene-1; m.p. 251° – 252°C, sol. 10%, (method E)

XXX 1-phenyl-2-benzyl-3-[4'-(β-piperidino-ethyl)-piperazino-1']-butene-1; m.p. 265° – 266°C, sol. 1%, (method E)

XXXI 1-phenyl-2-benzyl-3-[4'-(β-morpholino-ethyl)-piperazino-1']-butene-1; m.p. 266° – 267°C, sol. 10%, (method E)

XXXII 1-phenyl-2-benzyl-3- 4'-[β-(2-methylmorpholino)-ethyl]-piperazino-1' -butene-1; m.p. 251° – 252°C, sol. 10%, (method E)

XXXIII 1-phenyl-2-benzyl-3-[4'-(β-2''-methyl-piperidino-ethyl)-piperazino-1']-butene-1; m.p. 236.5°C, sol. 10%, (method E)

XXXIV 1-phenyl-2-benzyl-3- 4'-[β-(3''-methyl-piperidino)-ethyl]-piperazino-1' -butene-1; m.p. 233°C, sol. 2.5%, (method E)

XXXV 1-phenyl-2-benzyl-3- 4'-[β-(4''-methyl-piperidino)-ethyl]-piperazino-1' -butene-1; m.p. 272°C, sol. 1%, (method E)

XXXVI 1-phenyl-2-benzyl-3- 4'-[β(4''-methyl-piperazino-1''')-ethyl]-piperazino-1' -butene-1; m.p. 218°C, sol. <1%, (method E)

XXXVII 1-phenyl-2-benzyl-3- 4'-[β-(4''-benzyl-piperazino-1''')-ethyl]-piperazino-1' -butene-1; m.p. 254°C, sol. 5%, (method E)

XXXVIII 1-phenyl-2-benzyl-3- 4'-[β-(4''-α-phenethyl-piperazino-1''')-ethyl]-piperazino-1' -butene-1; m.p. 244°C, sol. 10%, (method E)

XXXIX 1-phenyl-2-benzyl-3- 4'-[β-(4''-β-phenethyl-piperazino-1''')-ethyl]-piperazino-1' -butene-1; m.p. 272°C, sol. 5%, (method E)

XL 1-phenyl-2-benzyl-3-[4'-(w-n-octyl-amino-n-hexyl)-piperazino-1']-butene-1; m.p. 256°C, sol. 1%, (method F)

XLI 1-phenyl-2-benzyl-3-[4'-(w-methyl-amino-n-hexyl)-piperazino-1']-butene-1; m.p. 202° – 204°C, sol. 10%, (method F)

XLII 1-p-chloro-phenyl-2-p-chloro-benzyl-3- 4'-[β-(4''-methyl-piperazino-1''')-ethyl]piperazino-1' -butene-1; m.p. 245°C, sol. 10%, (method E)

XLIII Dimethyl-n-octyl-β-[4-(1'-phenyl-2'-benzyl-butene-1'-yl-3')-piperazino-1]-ethyl-ammoniumbromide; m.p. 111° – 112°C, sol. <1%, (method C)

XLIV 1-phenyl-2-benzyl-3-(4'-β-chloro-ethyl-piperazino-1')-butene-1; m.p. 267° – 268°C, sol. 1%, (method F)

XLV 1-phenyl-2-benzyl-3-[4'-(β-chloro-ethyl)-piperazino-1']-butanol-2; m.p. 263° – 264°C, sol. 2.5%, (method B)

XLVI 1-phenyl-2-benzyl-3-[4'-(β-hydroxyethyl)-piperazino-1']-butanol-2; m.p. 234.5°C, sol. 10%, (method E)

XLVII 1-(p-Chloro-phenyl)-2-(p-chloro-benzyl)-3-[4'-(β-hydroxyethyl)-piperazino-1']-butanol-2; m.p. 251°C, sol. 10%, (method B)

XLVIII 1p-chlorophenyl-2-p-chlorobenzyl-3-(4'-methyl-piperazino-1')-butanol-2; m.p. 236° –237°C, sol. 5%, (method G)

IL 1-m-tolyl-2-(m-methyl-benzyl)-3-(4'-methyl-piperazino-1')-butanol-2; m.p. 240°C, sol. 5%, (method G)

L 1-phenyl-2-benzyl-3-piperazino-butanol-2; m.p. 221° – 223°C, sol. 1%, (method A)

LI 1-phenyl-2-benzyl-3-[1'-methyl-piperazino-4'-]-butanol-2; m.p. 245° –245.5°C, sol. 20%, (method G)

LII 1-phenyl-2-benzyl-3-(4'-phenyl-piperazino-1')-butanol-2; m.p. 239° – 240°C, sol. <1%, (method G)

LIII 1-phenyl-2-benzyl-3-(4'-benzyl-piperazino-1')-butanol-2; m.p. 234°C, sol. 1%, (method G)

LIV 1-phenyl-2-benzyl-3-(4'-m-methyl-benzyl-piperazino-1')-butanol-2; m.p. 215° – 217°C, sol. 1%, (method G)

LV 1-phenyl-2-benzyl-3-(4'-methyl-piperazino-1')-propanol-2; m.p. 246° – 247°C, sol. <2%, (method I)

LVI 1-phenyl-2-benzyl-4-(4'-methyl-piperazino-1')-butanol-2; m.p. 229°C, sol. 1%, (method H)

LVII 1-phenyl-2-benzyl-4-(4'-phenyl-piperazino-1')-butanol-2; m.p. 205° – 206°C, sol. <1%, (method H)

LVIII 1-phenyl-2-benzyl-3-(4'-methyl-piperazino-1')-pentanol-2; m.p. 244° – 246°C, sol. <1%, (method I)

LIX $\beta,\beta'$-diphenyl-$\beta''$-[4'-($\beta$-piperidino-ethyl)-piperazino-1']-t-butanol; m.p. 244° – 246°C, sol. 10%, (method I)

LX 1-phenyl-2-benzyl-4-[4'-($\beta$-piperidinoethyl)-piperazino-1']-butanol-2; m.p. 258° – 262°C, sol. 10%, (method H)

LXI 1-phenyl-2-benzyl-4- 4'-[w-(4''-methyl-piperazino-1'')-n-hexyl]-piperazino-1' -butanol-2; m.p. 288° – 290°C, sol. 10%, (method B)

LXII 1-phenyl-2-benzyl-3-[4'-w-(4''-n-octyl-piperazino-1'')-n-hexyl-piperazino-1']-butene-1; m.p. 260° – 262°C, sol. 2.5%, (method F)

LXIII 1(p-chloro-phenyl)-2-(p-chlorobenzyl)-4-[4'-($\beta$-piperidino-ethyl)-piperazino-1']-butene-1; m.p. 217.6°C, sol. <1%, (method H)

LXIV 1-phenyl-2-benzyl-4-[4'-($\beta$-piperidino-ethyl)-piperazino-1']-butene-1; m.p. 239° – 241°C, sol. 10%, (method H)

LXV 1-phenyl-2-benzyl-4-[4'-w-(4''-methyl-piperazino-1'')-n-hexyl-piperazino-1']-butene-1; m.p. 308° – 310°C, [D], sol. 10%, (method H)

LXVI 1-(o-chlorophenyl)-2-(o-chloro-benzyl)-3-[4'$\beta$-(4''-methyl-piperazino-1''')-ethyl-piperazino-1']-butene-1; m.p. 257° – 258°C [D], sol. 10% (method H)

LXVII hexahydro-azepinium-1-spiro-1'-piperazinium-4'-(3-benzyl-4-phenyl-but-3-en-2-yl)-chloride; m.p. 245°C, sol. 1%, (method F)

LXVIII 1-Phenyl-2-benzyl-4-piperazino-butanol-2. 2HCl, m.p. 185.6°C, solubility 10%, Method A.

LXIX 1-Phenyl-2-benzyl-3-(4'-n-octyl-piperazino-1')-butanol-2. 2HCl, m.p. 233.0°C, solubility 1%, Method G.

LXX 1-Phenyl-2-benzyl-3-[4'-(w-octyl-amino-n-hexyl)-piperazino-1']-butanol-2 . 3HCl, m.p. 236.0°C, solubility 2.5%, Method B. [Go 3436 A]

LXXI 1-Phenyl-2-benzyl-3-(4'-capryloyl-piperazino-1')-butanol-2 . HCl, m.p. 172.1°C, solubility 1%, Method A.

LXXII 1-Phenyl-2-benzyl-3-[4'-(w-piperidino-n-hexyl)-piperazino-1']-propanol-2 . 3HCl, m.p. 225.1°C, solubility 10%, Method B.

LXXIII 1-Phenyl-2-benzyl-3-[4'-[w-(4''-methyl-piperazino-1'')-n-hexyl]-piperazino-1']-propanol-2 . 4HCl, m.p. 282.5°C, solubility 10%, Method C.

LXXIV 1-Phenyl-2-benzyl-4-[4'-(w-piperidino-n-hexyl)-piperazino-1']butanol-2 . 3HCl, m.p. 258.6°C, solubility 10%, Method B.

LXXV Hexahydro-azepinium-1-spiro-1'-piperazinium-4'-(3-benzyl-4-phenyl-3-hydroxy-but-2-yl)-chloride, m.p. 242.6°C, solubility 2.5 %, Method B.

LXXVI 1-Phenyl-2-benzyl-3-[4'-(w-piperidino-n-hexyl)-piperazino-1']-propen-1 . 3 Oxalate, m.p. 203.7°C, solubility <1 %, Method F.

LXXVII 1-Phenyl-2-benzyl-4-[4'-(w-piperidino-n-hexyl)-piperazino-1']-buten-1 . 3HCl, m.p. 262.9°C (D), solubility 10 %, Method F.

LXXVIII

1-Phenyl-2-benzyl-2-acetoxy-4-[4'-(w-piperidino-n-hexyl)-piperazino-1']-butane 24 g (0.049 moles) 1-Phenyl-2-benzyl-4-[4'-(w-piperidino-n-hexyl)-piperazino-1']-butanol-2 were boiled for 8 hours in 100 ml acetic anhydride. After evaporation in a vacuum the residue was diluted in 100 ml water by adding a sufficient amount of potassium hydrogen carbonate. The basic ester obtained was extracted several times with a total amount of 1 Liter ether. The combined ether extracts after drying were saturated with dried hydrogen chloride. The oily residue of the 1-phenyl-2-benzyl-2-acetoxy-4-[4'-(w-piperidino-n-hexyl)-piperazino-1']-butane-trihydrochloride was separated from the supernatant ether and recrystallized from 400 ml and then from 150 ml isopropanol. Yield 18g (57 % o. th.), m.p. 260°C.

The melting points and solubilities are given for the Hydrochlorides I– XVI; XVIII – XXVII; XXIX – XXXV; XXXVII – XLII; XLIV – LXII; LXIV – LXVII, and the Oxalates, XVII; XVIII; XXXVI; LXIII.

Exemplary of the specific protocols used in making the novel compounds of this invention are the following examples:

EXAMPLE 1 (Method A)

1-Phenyl-2-benzyl-3- (4'-[$\beta$-(2''-methyl-piperidino)-ethyl]-piperazino-1' -butanol-2 [VII]

I. 52 g (0.3 M) of benzyl piperazine, 52 g (0.3 M) of $K_2CO_3$ and 56.3 g (0.3 M) of ethyl $\alpha$-bromopropionate are refluxed in 200 ml of alcohol for 16 hours. After separation of the inorganic salts by filtration, the alcoholic solution is evaporated and the residue dissolved in 1 l of water. The solution is acidified with HCl, extracted with 100 ml of ether, made alkaline and extracted with 3 portions of 250 ml of ether. The combined dried etheric solutions are evaporated and the residue is collected. Analysis of the residue shows: Yield: 67.7 g (82% of theoretical), b.p. (0.4 mm Hg) 138° – 141°C.

II. 15.6 g (0.65 gA) of magnesium are reacted with 75.9 g (0.6M) of benzyl chloride in 450 ml of absolute ether according to Grignard, refluxed for a quarter of an hour, cooled with ice water, and a solution of 67 g (0.25M) of ethyl $\alpha$-(4-benzyl-piperazino-1)-propionate in 500 ml of absolute ether is added and the mixture boiled for 6 hours. After cooling with ice water the Mg salt is decomposed with about 100 ml of ammonium chloride solution and the separated ether phase evaporated after drying. The residue is triturated with 50 ml of alcohol and crystallized from 500 ml of alcohol. Analysis of the 1-phenyl-2-benzyl-3-(4'-benzyl-piperazino-1')-butanol-2 crystals shows: Yield: 85 g (82% of theoretical), m.p. 106°–107°C. This is then dissolved in 1 l of ether and dry hydrogen chloride is passed through the solution until precipitation ceases. The hydrochloride is filtered off and crystallized from 300 ml of alcohol. Analysis of the product shows: Yield: 85.6 g (87% of theoretical), m.p. 254°C (decomp.).

III. g (0.16M) of 1-phenyl-2-benzyl-3-(4'-benzyl-piperazino-1')-butanol-2 . 2HCl are dissolved in 1.5 l of 50% methanol and hydrogenated over 8 g of 10% Pd-animal charcoal at a pressure of 30 atm. and a temperature of 20°C for 4 hours. After filtration of the catalyst the filtrate is evaporated to dryness and the residue crystallized from 0.5 l of alcohol. Analysis shows a yield of 44.5 g of the crude product. The product is dissolved in 0.5 l of water, the solution is made alkaline with NaOH, and the resulting precipitated base extracted with a total of 2 l of ether. The ether solution is dried and evaporated, and the residue crystallized from 250 ml of hexane. Analysis of the crystal base shows: Yield: 32.5 g (62.5% of theoretical), m.p. 106°–107°C.

IV. 0.7 g (0.1 gA) of Li are added to a solution of 23.4 g (0.1M) of bromobenzene in 400 ml of absolute ether, and the solution is stirred under nitrogen gas until dissolved. The solution, filtered free of LiBr, is added to a solution of 16.3 g (0.05M) of 1-phenyl-2-benzyl-3-piperazino-butanol-2 in 100 ml of absolute toluene. The ether is distilled off (until the b.p. of toluene is reached at 108°) at which time the solution is diluted with 300 ml of absolute toluene. 8.08 (0.05M) of 2-methyl-piperidino ethyl-chloride are added, as droplets, to this solution with boiling and the solution refluxed for 8 hours. After filtration of the formed LiCl, toluene is removed in vacuo and the residue extracted several times with a total of 1 l of ether. The etheric solution is saturated with dry hydrogen chloride, the hydrochloride salt filtered off and crystallized from about 400 ml of isopropanol. Analysis of the crystals show: Yield: 5.4 g (18% of theoretical), m.p. 234°–236°C.

EXAMPLE 2 (Method B)

1-Phenyl-2-benzyl-3-[4'-(w-piperidino-n-hexyl)-piperazino-1']-butanol-2 [XX]

I. To 172 g (2M) of piperazine (anhydrous) is added over 1 hour a solution of 136.5 g (1M) of 6-chlorohexanol-1 in 400 ml of ethanol at 75°C, and the mixture is refluxed for 15 hours. After evaporation the residue is fractionated, and analysis of the product shows: Yield: 80 g (43% of theoretical), b.p. (0.2 mm Hg) 124°–126°C.

II. To 77 g (0.41M) of 6-piperazino-hexanol-1, dissolved in 250 ml of ethanol is added, dropwise, a solution of 63 g (0.41M) of ethyl α-bromo-propionate in 100 ml of ethanol. The mixture is boiled, stirred, and refluxed for 16 hours with continuous stirring. After evaporation a syrupy residue is obtained. Analysis of this residue shows: yield: (crude) 135 g (97.5% of theoretical).

III. To 135 g (0.4M) of crude ethyl α-[4-(w-hydroxy-n-hexyl)-piperazino]-propionate . HBr in 250 ml of chloroform is added, dropwise, with stirring 100 ml (1.3M) of thionylchloride at room temperature. The mixture is refluxed with stirring for 8 hours, evaporated, and the residue is stirred with 1 l of ether. The crystalline product is filtered off and crystallized from 500 ml of isopropanol. Analysis shows: Yield: 84 g (55% of theoretical) m.p.: 185°C.

IV. 60 g (0.2M) of ethyl α-[4-(w-chloro-n-hexyl)-piperazino]-propionate, obtained from 84 g (0.22M) of the hydrochloride salt dissolved in 1 l of dried ether, are added dropwise to a Grignard solution of 36.5 g (1.5 gA) of magnesium and 190 g (1.5M) of benzyl chloride in 300 ml of dried ether and the solution is refluxed for 16 hours with stirring. While cooling with ice a saturated ammonium chloride solution is added (about 250 ml) until a granulated precipitate is obtained. After filtration and washing with ether the combined etheric phases are dried and saturated with dry hydrogen chloride. The hydrochloride is filtered off and crystallized from 1 l of ethanol. Analysis of the crystaline product shows: Yield: 60 g (58% of theoretical) m.p.: 244°–246°C.

V. 20 g (0.04m) of 1-phenyl-2-benzyl-3-[4'-(w-chloro-n-hexyl)-piperazino]-butanol-2 . 2 HCl are refluxed in 200 ml of piperidine for 16 hours with stirring. After cooling and filtering from the piperidine-HCl the filtrate is evaporated in vacuo, the residue dissolved in 500 ml of ether, filtered, and saturated with dry hydrogen chloride. The hydrochloride is filtered off and crystallized twice from portions of 250 ml and once from 150 ml of n-propanol. Analysis of the resulting product shows: Yield: 10.5 g (42.5% theoretical), m.p.: 243°C.

EXAMPLE 3 (Method C)

1-Phenyl-2-benzyl-3-[1'-(β-dimethylamino-ethyl)-piperazino-4']-butanol-2 [I]

I. 65.2 g (0.2M) of ethyl α-[4-(β-chloro-ethyl)-piperazine-1]-propionate dihydrochloride are heated with 250 ml of condensed dimethylamine to 80°C for 8 hours in a 500-ml glass autoclave. After evaporation of excessive dimethylamine the residue is mixed with 1 l of ether, filtered off from dimethylamine hydrochloride and the filtrate saturated with dry hydrogen chloride. It is then filtered and crystallized from 800 ml of a 1 : 1 mixture of ethanol/ethyl acetate. Anaylsis shows: Yield: 62 g (83.5% of theoretical), m.p. 213°–214°C (Decomp.)

II. 24.3 g (0.1 gA) of magnesium chips are reacted with 126.6 g (1 M) of benzyl chloride in 1 l of absolute ether according to Grignard, and 33 g (0.128 M) of ethyl α-[4-(β-dimethylamino-ethyl)-piperazino-1]-propionate (released from the dihydrochloride salt with potassium hydrogen carbonate dissolved in 1.2 l of dried ether) are added dropwise. After having refluxed for 8 hours, the mixture is cooled with stirring and about 200 ml of saturated ammonium chloride solution are carefully added until the finely crystalline precipitate has completely changed into a coarse precipitate. The precipitate is filtered off, washed with 200 ml of ether and the combined etheric phase are dried and saturated with dry hydrogen chloride. For removing the starting ester which has not reacted, the filtered hydrochloride is refluxed in a solution of 112 g of KOH in 500 ml of methanol, evaporated, triturated with 150 ml of water and extracted with 1.5 l of ether. The dried etheric phase is saturated with dry hydrogen chloride and the filtered hydrochloride crystallized twice from portions of 700 ml of ethanol. Analysis shows: Yield: 14 g (21.5% of theoretical), m.p. 263°–264°C.

EXAMPLE 4 (Method D)

1-Phenyl-2-benzyl-3-[4'-(β-morpholino ethyl)-piperazino-1']-butanol-2 [V]

I. 250 g (1.6 M) of N-(β-hydroxyethyl)-piperazine are dissolved in 1 l of ethanol and precipitated as the dihydrochloride salt by passing into the solution dry hydrogen chloride gas. Analysis shows: Yield: 380 g (99% of theoretical) of crude product. 380 g (1.6 M) of crude N-(β-hydroxyethyl)-piperazine dihydrochloride are refluxed with stirring in 2.5 l of thionylchloride for 6 hours. After evaporating the thionylchloride on a steam bath in vacuo the residue is extracted with 4 l of boiling ethanol, cooled, and filtered. Analysis shows: Yield: 365 g (92% of theoretical), m.p. 229°–231°C. (By crystallization from about 1% etheric solution the m.p. increases to 231°–232°C.).

II. 28.8 g (0.13 M) of N-piperazino ethyl-chloride dihydrochloride are refluxed in 150 ml of morpholine for 6 hours, and the non-reacted morpholine evaporated on a steam bath in vacuo. The residue is taken up in 500 ml of ether, filtered from the morpholine hydrochloride and the filtrate evaporated. The syrupy residue is then fractionated in high vacuum. Analysis of the residue shows: Yield: 12 g (46% of theoretical), b.p. (0.5 mm Hg) 92°.

III. 59.8 g (0.3 M) of $\beta$-morpholino ethyl-piperazine are refluxed with 54.3 g (0.3 M) of ethyl $\alpha$-bromopropionate in 100 ml of ethanol for 20 hours. The product is then evaporated and an oily residue is extracted with 2 l of boiling ethylacetate. The extracted crystalline product is filtered and crystallized from 2 l of a 1 : 1 mixture of ethyl acetate/ethanol. Analysis of this product shows: Yield: 60 g (52.5% of theoretical), m.p. 227° – 228°C. 60 g (0.158 M) of N-($\beta$-morpholino ethyl)-N'-($\alpha$-carbethoxy-ethyl)-piperazine hydrobromide are dissolved in 150 ml of water, mixed with 50 g of sodium hydrogencarbonate. The released base is extracted with 3 l of ether, dried and the solvent evaporated. Analysis of the product shows: Yield: 39.5 g (83.6% of theoretical) of oily product.

IV. A solution of 39.5 g (0.132 M) of crude ethyl $\alpha$-[4-($\beta$'-morpholino ethyl)-piperazino-1]-propionate in 700 ml of absolute ether is added dropwise to a Grignard solution of 18.2 g (0.75 gA) of magnesium chips and 95 g (0.75 M) of benzyl chloride in 500 ml of absolute ether. The mixture is refluxed for 6 hours with stirring. After cooling in an ice bath, a saturated ammonium chloride solution is added (about 190 ml) until the microcrystalline precipitate has changed into a grained precipitate. The solution is filtered, the residue washed with 200 ml of ether, and the combined dried ether phases are saturated with dry hydrogen chloride. The hydrochloride salt formed is filtered and crystallized first from 1.2 l, then from 600 ml of ethanol. Analysis of the resultant product shows: Yield: 27 g (39.5% of theoretical), m.p.: 246.5°C.

EXAMPLE 5 (Method E)

1-Phenyl-2-benzyl-3-[4'-($\beta$-diethylamino-ethyl)-piperazino-1']-butene-1 [XXVII]

I. 39 g (0.17 M) of ethyl $\alpha$-(4-$\beta$-hydroxyethyl-piperazino-1-)-propionate (produced from 53.9 g of the hydrobromide salt by sodium hydrogen carbonate) in 700 ml of absolute ether, are added dropwise to the Grignard solution of 18.25 g (0.7 gA) of magnesium and 88.5 g (0.7 M) of benzyl chloride in 300 ml of absolute ether. After refluxing for 3 hours, the mixture is cooled, a saturated ammonium chloride solution added until an aqueous phase is observed (about 200 ml), filtered from the precipitate and saturated with dry hydrogen chloride. The filtered hydrochloride is crystallized from 500 ml of a 4 : 1 mixture of ethanol/isopropanol. Analysis of the product shows: Yield: 35.1 g (47% of theoretical), m.p.: 230°C.

II. 44 g (0.1 M) of 1-phenyl-2-benzyl-3-[4'-($\beta$-hydroxyethyl)-piperazino-1']-butanol-2 . 2HCl are refluxed in 500 ml of thionylchloride for 4 hours. The insoluble product is filtered after cooling and crystallized from 500 ml of ethanol. Analysis of the crystallized product shows: Yield: 8.8 g (20% of theoretical), m.p. 267° – 268°C (decomp.)

III. 20.7 g (0.045 M) of 1-phenyl-2-benzyl-3-(4'-$\beta$-chloroethyl-piperazino)-butene-1 dihydrochloride are refluxed for 10 hours with stirring in 200 ml of methanol with 18.3 g (0.25 M) of diethylamine. After evaporation of the methanol, the mixture is triturated with 1 l of ether, filtered from diethylamine hydrochloride and the etheric filtrate is saturated with dry hydrogen chloride. The filtered hydrochloride is crystallized twice from 1 l of a 1 : 4 mixture of ethanol/ethyl acetate. Analysis of the final product shows: Yield: 13.7 g (56% of theoretical) m.p. 187° – 188°C.

EXAMPLE 6 (Method F)

1-Phenyl-2-benzyl-3-[4'-(w-n-octyl-amino-n-hexyl)-piperazino-1']-butene-1 [XL]

I. 40 g (0.08 M) of 1-phenyl-2-benzyl-3-[4'-(w-chloro-n-hexyl)-piperazino-1']-butanol-2 . 2HCl are added to a mixture of 100 ml of thionylchloride and 100 ml of $CCl_4$ and refluxed with stirring for 3 hours. After evaporating not quite to dryness, 100 ml of $CCl_4$ are added, and evaporated again. This operation is repeated twice. The residue is collected by suction, dissolved in 300 ml of ethanol, and evaporated as before. The residue is then mixed with 300 ml of ether and collected. Yield: 35 g (crude)

II. 45 g (0.09 M) of crude 1-phenyl-2-benzyl-3-[4'-($\omega$-chloro-n-hexyl)-piperazino-1']-butene-1 . 2 HCl are suspended in 250 ml of n-propanol containing 1 g of potassium iodide and 45 g (0.36 M) of n-octylamine and refluxed with stirring for 16 hours. After evaporation the residue is extracted with 500 ml of ether, filtered from octylamine HCl and saturated with dry hydrogen chloride. The filtered hydrochloride is boiled twice with 200 ml of ethyl acetate, filtered and crystallized from a 1 : 2 mixture of ethanol/ethyl acetate. Analysis of the final product shows: Yield: 6.4 g (11% of theoretical), m.p. 256°C.

EXAMPLE 7 (Method G)

1-p-Chlorophenyl-2-p-chlorobenzyl-3-(4'-methyl-piperazino-1')-butanol-2 [XLVIII]

I. 50 g (0.5 M) of N-methyl-piperazine are heated on a steam bath and 45 g (0.25 M) of ethyl $\alpha$-bromo-propionate are added dropwise while stirring vigorously. Stirring is continued for about a quarter of an hour while heating. The mixture is cooled and allowed to stand overnight. It is then triturated several times with a total of 1.5 l of ether and resuspended in and filtered from methyl-piperazine . HBr. The ether is evaporated and the residue fractioned in high vacuum. Analysis of the intermediate product shows: Yield: 36 g (71% of theoretical), b.p. (0.1 – 0.3 mm Hg) 73°–73.5°C.

II. 7.2 g (0.3 gA) of magnesium are reacted with 48 g (0.3 M) of p-chlorobenzylchloride in 350 ml of absolute ether, according to Grignard, and refluxed for a quarter of an hour. While cooling with ice a solution of 20 g (0.1 M) of ethyl $\alpha$-(methyl-piperazino-1)-propionate in 500 ml of absolute ether is added dropwise to the primary mixture above and refluxed for 10 hours. While the secondary mixture is cooling with ice the magnesium salt is decomposed with 80 ml of saturated ammonium chloride solution and the separated dried ether phase is treated with charcoal and saturated with dry hydrogen chloride. The supernatant ether is decanted from the oily hydrochloride. The oil is crystallized by trituration with 20 ml of ethanol, filtered and crystallized twice from two 150 ml solutions of ethanol. Analysis of the final product shows: Yield: 13 g (26% of theoretical) m.p. 236° – 237°C.

EXAMPLE 8 (Method H)

1-Phenyl-2-benzyl-4-(4'-methyl-piperazino-1')-butanol-2 [LVII]

I. 12.5 g (0.125 M) of N-methylpiperazine are added while cooling with ice to 12.5 g (0.125 M) of ethyl acrylate and allowed to stand for 120 hours at room temperature. Then the mixture is fractionated in vacuo. Results of the analysis of this product show: Yield: 23.4 g (93.5% of theoretical) b.p. (12 mm Hg) 127° – 130°C.

II. 9.6 g (0.4 gA) of magnesium chips are reacted with 44.1 g (0.35 M) of benzyl chloride in 400 ml of absolute ether according to Grignard, and the mixture refluxed for a quarter of an hour. After cooling with ice a solution of 20 g (0.1 M) of ethyl β-(4-methyl-piperazino-1)-propionate in 400 ml of absolute ether is added dropwise and refluxed for 10 hours. While cooling the resultant product with ice, the magnesium salt is decomposed with 70 ml of saturated ammonium chloride solution, and the separated dried ether phase is saturated with dry hydrogen chloride and filtered. The resulting hydrochloride is crystallized twice from two 750 ml solutions of absolute ethanol. Analysis of the final product shows: Yield: 20 g (48.5% of theoretical) m.p. 229°C (decomp.)

EXAMPLE 9 (Method I)

1-Phenyl-2-benzyl-3-(4'-methyl-piperazino-1')-pentanol-2 [LVIII]

I. 50 g (0.5 M) of N-methylpiperazine, 98 g (0.5 M) of ethyl α-bromo-butyrate and 40 g (0.29 M) of potassium carbonate (anhydrous) are refluxed and stirred overnight in 250 ml of ethanol. After cooling, the mixture is filtered and the solvent evaporated in vacuo. The residue is mixed with 1 l of water and extracted with ether. After drying the separated ether phase over sodium sulfate, the solvent is evaporated and the residue column-fractionated. Analysis of the product shows: Yield: 43 g (40% of theoretical), b.p. (12 mm Hg) 127° – 128°C.

II. 38 g (0.3 M) of benzyl chloride are reacted with 8 g (0.35 gA) of Mg in 150 ml of absolute ether. While this is cooling with ice, a solution of 21.4 g (0.1 M) of ethyl α-(4-methylpiperazino-1)-butyrate in 500 ml of absolute ether is added and the mixture is refluxed for 20 hours. While cooling the mixture, the magnesium salt is decomposed with about 75 ml of saturated ammonium chloride solution and the ether solution is decanted from the precipitate. The dried ether solution is saturated with dry hydrogen chloride and filtered. The resulting hydrochloride is crystallized twice from two 250 ml solutions of ethanol. Analysis of the product so obtained shows: Yield: 29 g (68.4% of theoretical), m.p. 244° – 246°C.

EXAMPLE 10 (Method C)

Dimethyl-n-octyl-β-[4-(1'-phenyl-2-benzyl-butene-1'-yl-3')-piperazino-1]-ethyl ammonium-bromide [XLIII]

28 g (0.057 m) of 1-phenyl-2-benzyl-3-[4'-(β-dimethylamino-ethyl)-piperazino-1']-butene-1 . 3HCl are dissolved in 500 ml of water, about 50 g of potassium bicarbonate are added and the mixture is extracted with 1 l of ether. The etheric solution is dried and evaporated. The residue [21 g, (0.055 M)] is dissolved in 200 ml of absolute ethanol containing 10.5 g (0.055 M) of octylbromide and refluxed for 5 hours. The solvent is evaporated and the residue allowed to crystallize overnight. Recrystallization from 200 ml of ethyl acetate is done to obtain a purified product which upon analysis shows: Yield: 13 g (41.5% of theoretical), m.p. 111° – 112°C.

EXAMPLE 11 (Method E)

1-Phenyl-2-benzyl-3- 4'-[4''-methyl-piperazino-1''-ethyl]-piperazino-1' -butene-1 [XXXVI]

40.6 (0.092 M) of 1-phenyl-2-benzyl-3-[4'-(β-chloro-ethyl)-piperazino-1']-butene-1 (see Example 5/II) are refluxed in a 200 ml of ethanol solution containing 18 g (0.18 M) of N-methylpiperazine for 5 hours with stirring. After evaporation of the ethanol, the residue is triturated with 1 l of diethyl-ether, filtered, and to the ether filtrate is added a saturated and dried solution of oxalic acid in diethyl-ether until precipitation is completed. The filtered product is crystallized twice from 1.2 l of water each time. Analysis of the product shows: Yield: 15 g (20% of theoretical), m.p. 118°–119°C.

EXAMPLE 12 (Method H)

1-Phenyl-2-benzyl-4-[4'-(β-piperidino-ethyl)-piperazino-1']-butanol-2 [LX]

I 110.8 g (0.5 M) of N-piperazino-ethyl-chloride dihydrochloride are refluxed with stirring in a 600 ml piperidine solution containing 0.1 g of potassium iodide for 10 hours. After cooling, the piperidine hydrochloride is filtered and the filtrate evaporated in vacuo. The residue is taken up in 500 ml of ether, filtered, the filtrate evaporated, and the residue is fractionated in high vacuum. (b.p. (0.1 mm HG) 82°–84°C)

II 50 g (0.25 M) of N-(β-piperidino-ethyl)-piperazine are added (with cooling by ice) to 25.3 g (0.25 M) of ethyl acrylate. After standing at room temperature for 130 hours the mixture is fractionated in high vacuum. (b.p. (0.6 mm HG) 140° – 150°C).

III 65.6 g (0.22 M) ethyl β-[4-(β-piperidino-ethyl)-piperazino-1]-propionate in 500 ml of absolute diethylether are added dropwise (while cooling with ice) to a Grignard solution of 32.1 g (1.32 gA) of magnesium and 167.2 g (1.32 M) of benzyl chloride in 300 ml of absolute ether. After refluxing and stirring for 18 hours the mixture is cooled by ice and a saturated ammonium chloride solution is added dropwise until an aqueous phase is observed (about 300 ml). The etheric phase is filtered from the precipitate and saturated with dry hydrogen chloride. The filtered hydrochloride salt is refluxed in 600 ml of 10% methanolic potassium hydroxide for one hour, the solvent evaporated, and the residue dissolved in 200 ml of water. The aqueous solution is extracted several times with a total of 1 l of ether. The combined etheric phases are dried and saturated with dry hydrogen chloride. The filtered hydrochloride salt is first crystallized from a mixture of 440 ml of isopropanol and 400 ml of methanol and then twice more from 220 ml of ethanol. Analysis of the product shows: Yield: 17.6 g (15% of theoretical), m.p. 258° – 262°C.

EXAMPLE 13 (Method H)

1-Phenyl-2-benzyl-4-[4'-(β-piperidino-ethyl)-piperazino-1']-butene-1 [LXIV]

30 g (0.055 M) of 1-phenyl-2-benzyl-4-[4'-(β-piperidino-ethyl)-piperazino-1']-butanol-2 (Example 12) are added in small portions to 150 ml of thionylchloride and refluxed with stirring for 5 hours. Half the amount of the thionyl-chloride is evaporated and 150 ml of carbon tetrachloride are added to the residue and evaporated with stirring. This operation is repeated three times. After evaporating to dryness, the residue is recrystallized twice, once from 700 ml of ethanol and then from 400 ml of ethanol. Analysis of the product show: Yield: 9.7 g (32.7% of theoretical), m.p. 270° – 272°C.

EXAMPLE 14 (Method B)

1-Phenyl-2-benzyl-4-[4'-w-(4''-methyl-piperazino-1'')-n-hexyl-piperazino-1']-butanol-2 [LXI]

I To 56 g (0.3 M) of 6-piperazino-hexanol-1 are slowly added, with shaking and cooling with ice, 30 g (0.3 M) of ethyl acrylate. After standing at room temperature for 145 hours the mixture is fractionated in high vacuum. Analysis of the intermediate product shows: Yield: 69.5 g (93% of theoretical), b.p. 0.01 160° – 180°C.

II 69g (0.27M) of ethyl β-(4-w-hydroxy-hexyl-piperazino-1)-propionate are dissolved in 500 ml of chloroform and the solution saturated with dry hydrogen chloride to precipitate the salt. To this suspension, 100 ml of thionyl chloride are added and the mixture is refluxed, with stirring, for 2 hours. To this solution is added 200 ml of carbon tetrachloride and the solvent containing the thionyl chloride is evaporated. This operation is repeated twice. The residue is finally suspended in 300 ml of carbon tetrachloride, filtered, and washed with 100 ml of carbon tetrachloride and 100 ml of ether. Analysis of the material shows: 87 g (85.5% of theoretical), m.p. 218°C.

III 64 g (0.21 M) of the crude ethyl β-(4-w-chlorohexyl-piperazino-1)-propionate in 800 ml of dry diethylether are added slowly with cooling by ice to a Grignard solution of 73 g (3 gA) magnesium and 380 g (3 M) benzyl chloride in 1 l of dry ether, and the mixture is then refluxed with stirring for 20 hours. While cooling with ice a saturated ammonium chloride solution is added dropwise to the mixture until a granulated precipitate is obtained (about 650 ml). After filtering and washing with ether, the combined etheric phases are dried and saturated with dry hydrogen chloride. The filtered hydrochloride salt is recrystallized from 1.1 l of isopropanol.

IV 59 g (0.115 M) of 1-phenyl-2-benzyl-4-[4'-w-chloro-hexyl-piperazino-1')-butanol-2 are added in small portions with stirring to 250 ml of N-methyl-piperazine and the mixture is refluxed with stirring for 40 hours. After cooling, the N-methyl-piperazine is filtered off and the filtrate evaporated. The residue is then triturated with 3 l of ether and filtered from the remaining N-methyl-piperazine. The filtrate is saturated with dry hydrogen chloride, filtered, and recrystallized from 1.5 l of 90% ethanol. Analysis of the final product shows: Yield: 31.8 g (42% of theoretical), m.p. 288° – 290°C (decomp.)

EXAMPLE 15 (Method H)

1-Phenyl-2-benzyl-4-[4'-w-methyl-piperazino-1''')-n-hexyl-piperazino-1']-butene-1 [LXV]

23 g (0.035 M) of 1-phenyl-2-benzyl-4-[4'-w-(4''-methylpiperazino-1''')-n-hexyl-piperazino-1'[-butanol-2 (Example 14) are added to 160 ml of thionylchloride, and the mixture is refluxed for 4.5 hours.

After evaporating the thionylchloride, the residue is triturated with 200 ml of carbon tetrachloride. The solvent is evaporated and this operation is repeated. The residue is triturated with 250 ml of boiling ethanol, cooled, and the crystallized product is filtered and recrystallized from 650 ml of ethyleneglycol monomethyl ether. Analysis of the final product shows: Yield: 14.5 g (63.5% of theoretical) m.p. 308° – 310°C (decomp.)

EXAMPLE 16 (Method F)

1-Phenyl-2-benzyl-3-[4'-(w-methyl-amino-n-hexyl)-piperazino-1']-butene-1 [XLI]

25 g (0.05 M) of crude 1-phenyl-2-benzyl-3-[4'-(3-chloro-n-hexyl)-piperazino-1']-butene-1 are added in small portions to 100 ml of condensed methyl amine at temperatures between −30 to −20°C in a glass autoclave. After closing of the autoclave the mixture is heated to 80°C for 16 hours. After cooling to −10°C the autoclave is opened and the methylamine is evaporated at room temperature. The residue is triturated with 200 ml of diethylether and filtered from the methylamine hydrochloride. The filtrate is saturated with dry hydrogen chloride and the filtered hydrochloride salt is recrytallized from a 1 : 1 mixture of ethanol and ethyl acetate. Analysis of the final product shows: Yield: 5.3 g (20% of theoretical), m.p. 202° – 204°C.

The following list contains further examples of those compounds which are made according to the methods disclosed:

1-o-Chloro-phenyl-2o-chloro-benzyl-4-[4'-(w-n-octyl-amino-n-hexyl)-piperazino-1'-]-butene-1, 1-p-hydroxy-phenyl-2-p-hydroxy-benzyl-4-[4'-(w-n-octyl-amino-n-hexyl)-piperazino-1']-butene-1; 1-(m-N,N-diethyl-anilino)-2-(m-diethylamino-benzyl)-4-[4'-(w-n-octyl-amino-n-hexyl)-piperazino-1']-butene-1; 1-(p-n-butyl-phenyl)-2-(p-n-butyl-benzyl)-4-[4'-(w-n-octyl-amino-n-hexyl)-piperazino-1']-butene-1; 1-(p-n-butoxy-phenyl)-2-(p-n-butoxy-benzyl)-3-[4'-(w-n-octyl-amino-n-hexyl)-piperazino-1']-butene-1; 1-(p-but-2'-en-1'-yl-phenyl)-2-(p-but-2'-en-1'-yl-benzyl)-4-[4'-(w-n-octyl-amino-n-hexyl)-piperazino-1']-butene-1; 1-(m-but-3'-in-1'-oxy-phenyl)-2-(m-but-3'-in-1'-oxy-benzyl)-3-[4'-(w-n-octyl-amino-n-hexyl)-piperazino-1']-butene-1; 1-(o-ethyl-mercapto-phenyl)-2-(o-ethyl-mercapto-benzyl)-4-[4'-(w-n-octyl-amino-hexyl)-piperazino-1']-butene-1; 1-(p-w-hydroxy-butyl-phenyl)-2-(p-w-hydroxy-butyl-benzyl)-4-[4'-(w-n-octyl-amino-n-hexyl)-piperazino-1']-butene-1; 1-(p-w-amino-propyl-phenyl)-2-(p-w-amino-propyl-benzyl)-4-[4'-(w-n-octyl-amino-n-hexyl)-piperazino-1']-butene-1; 1-(m-β-chloro-ethyl-phenyl)-2-(m-β-chloroethyl-benzyl)-4-[4'-(w-n-octyl-amino-n-hexyl)-piperazino-1']-butene-1; 1-(2'-pyridyl)-2-(2'-picolyl)-4-[4'-(w-n-octyl-amino-n-hexyl)-piperazino-1']-butene-1; 1-(6'-pyrimidyl)-2-(6'-pyrimidyl-methyl)-4-[4'-(w-n-octyl-amino-n-hexyl)-piperazino-1']-butene-1; 1-(2'-furyl)-2-(2'-furfuryl)-3-[4'-(w-n-octyl-amino-n-hexyl)-piperazino-1']-butanol-2; 1-(2'-thienyl)-2-(2'-thenyl)-

4-[4'-(w-n-octyl-amino-n-hexyl)-piperazino-1']-butanol-2; 1-methyl-1-phenyl-2-α-phenethyl-3-[4'-(w-methyl-amino-n-hexyl)-piperazino-1']-butanol-2; 1-butyl-1-phenyl-2-(α-phenyl-n-butyl)-4-[4'-(β-piperidinoethyl)-piperazino-1']-butene-1; 1-phenyl-2-benzyl-3-[4'-(w-n-octyl-amino-n-hexyl)-piperazino-1']-butane; 1-phenyl-2-benzyl-4-[4'-(β-dimethyl-amino-ethyl)piperazino-1']-butyl-2-ethylether; 1-phenyl-2-benzyl-3-[4'-(w-methyl-amino-n-hexyl)-piperazino-1']-butyl-2 n-butyrate; 1-phenyl-2-benzyl-3-methyl-3-[4'-(w-n-octyl-amino-n-hexyl)-piperazino-1']-butanol-2; 1-phenyl-2-benzyl-4-[4'-(w-methyl-amino-n-hexyl)-2',3',5', 6'-tetra-methyl-piperazino-1']-butene-1; 1-phenyl-2-benzyl-4-[4'-(β-morpholino-ethyl)-2',3'-pentamethylen-piperazino-1']-butene-1; 1-phenyl-2-benzyl-3-[4'-(w-methyl-amino-deca-5'', 8''-dienyl)-piperazino-1']-butene-1; 1-phenyl-2-benzyl-3-[4'-(3''-ethyl-4''-n-octyl-amino)-piperazino-1']-butene-1; 1-phenyl-2-benzyl-4-[4'-(β-p-N-methyl-anilino-ethyl)-piperazino-1']-butanol-2; 1-phenyl-2-benzyl-3- 4'-[4''-(n-octyl-amino-cyclohexyl-1'']-piperazino-1' -butene-1; 1-phenyl-2-benzyl-4-[4'-(β-ethoxy-ethyl)-piperazino-1']-butene-1; 1-phenyl-2-benzyl-3-[4'-(β-propionoxy-ethyl)-piperazino-1']-butanol-2; 1-phenyl-2-benzyl-4-[4'-(w-3''-ethyl-dodeca-2''-en-1''-yl-amino-n-hexyl)-piperazino-1']-butene-1; 1-phenyl-2-benzyl-4-[4'-(w-cyclohexylamino-hexyl)-piperazino-1']-butene-1; 1-phenyl-2-benzyl-4-[4'-(β-phenethyl-amino)-piperazino-1']-butene-1; 1-phenyl-2-benzyl-3-(4'-p-hydroxy-phenyl)-piperazino-1']-butanol-2; 1-phenyl-2-benzyl-3-[4'-(β-p-N,N-dimethyl-anilino-ethyl)-piperazino-1']-butene-1; 1-phenyl-2-benzyl-3- 4'-[w-(4''-methyl-piperazino-1'''-n-hexyl-amino)-n-hexyl]-piperazino-1' -butene-1; 1-phenyl-2-benzyl-3-[4'-β-(β'-chloro-ethyl-azo)-ethyl-piperazino-1']-butene-1; 1-phenyl-2-benzyl-4-[4'-w-(w'-ethoxy-n-hexyl-N'-hydrazino-N)-n-hexyl-piperazino-1']-butene-1; 1-phenyl-2-benzyl-4-[4'-β-(w''-phenoxy-hexyliden-1''-imino)-ethyl-piperazino-1']-butene-1; 1-phenyl-2-benzyl-3-[4'-β-(4''-phenyl-piperidino-1''')-ethyl-piperazino-1'']-butene-1; 1-phenyl-2-benzyl-4-[4'-w-(4'''-β-phenethyl-piperidino-1''')-n-hexyl-piperazino-1']-butene-1; 1-phenyl-2-benzyl-4-[4'-w-(5''-n-octyl-biguanidyl-1''')-n-hexyl-piperazino-1']-butene-1.

The results of the antimicrobial activity tests of representative compounds of the invention are illustrated by the following examples:

EXAMPLE 17

The efficacy of the compounds against Mycobacteria was tested in the following way:

A Tb-broth according to DUBOS (DUBOS, R. J., Proc. Soc. Exp. Biol. Med. 58: 531 (1945)) was supplemented by adding 10% of bovine serum and used in the preparation of a standard dilution series of the compounds to be tested. The dilution series was inoculated with a photometrically adjusted standard suspension of *Mycobacterium tuberculosis II* 37 RV (typus humanus) and incubated at 37° for 21 days.

Concentrations were reported as minimum inhibitory concentrations (MIC), that is those concentrations which inhibited visible growth of the bacteria after 21 days.

The MIC in micrograms per ml of a representative number of compounds of this invention are found in Table I.

TABLE I

| Compound No. | Minimum Inhibitory Concentration in $\mu$g/ml | Compound No. | Minimum Inhibitory Concentration in $\mu$g/ml |
|---|---|---|---|
| III | 50 | XXV | 10 |
| IV | 100 | XXVII | 10 |
| V | 100 | XXIX | 10 |
| VI | 100 | XXX | 50 |
| VII | 10 | XXXII | 50 |
| VIII | 100 | XXXIII | 20 |
| IX | 100 | XLV | 100 |
| XII | 100 | IL | 100 |
| XIX | 100 | L | 500 |
| XXII | 500 | LVIII | 100 |
| XXIII | 1000 | | |

EXAMPLE 18

The efficacy of the compounds against fungi was tested as follows:

Using a suitable solvent for the respective compound but non toxic to fungi, preferably a 1/15M phosphate buffer having a pH of 7.2, solutions were prepared containing a 10.0 mg, 1.0 mg and 0.1 mg per ml of the compound to be tested. The test organisms, in this case the blastomycete *Candida albicans* and the mold *Aspergillus niger*, were inoculated onto Sabouraud agar plates by pouring a photometrically adjusted standard suspension of organisms on the plate. After inoculation, wells with a diameter of 5.0 mm were punched in the agar, and filled with 50 $\mu$l of the compound solution mentioned before. The quantity of compound applied thus amounted to 500 $\mu$g, 50 $\mu$g and 5 $\mu$g. After incubation at 28° for 48 hours, the quantity of compound was determined at which an inhibition of the organism's growth, in form of an inhibition zone around the corresponding well, was present.

The concentrations at which zones of inhibition occurred for all of the compounds of this invention are found in Table II:

TABLE II

| Compound No. | Inhibition Area at $\mu$g | | Compound No. | Inhibition Area at n $\mu$g | |
|---|---|---|---|---|---|
| | Cand. albicans | Asp. niger | | Cand. albicans | Asp. niger |
| I | 50 | 50 | XV | 50 | 50 |
| II | 50 | 50 | XVI | >500 | >500 |
| III | 50 | 50 | XVII | 500 | 500 |
| IV | 50 | 500 | XVIII | >500 | >500 |

TABLE II-continued

| Compound No. | Inhibition Area at μg Cand. albicans | Asp. niger | Compound No. | Inhibition Area at n μg Cand. albicans | Asp. niger |
|---|---|---|---|---|---|
| V | 50 | 50 | XIX | 5 | 5 |
| VI | 500 | 500 | XX | 50 | 5 |
| VII | 50 | 500 | XXI | 50 | 5 |
| VIII | 50 | 500 | XXII | 500 | 500 |
| IX | 50 | 50 | XXIII | 500 | >500 |
| X | 50 | 50 | XXIV | >500 | >500 |
| XI | 50 | 500 | XXV | 5 | 5 |
| XII | 5 | 50 | XXVI | 5 | 5 |
| XIII | 500 | 500 | XXVII | 5 | 5 |
| XIV | 50 | 50 | XXVIII | 50 | 50 |
| XXIX | 50 | 50 | XLVII | 5 | 5 |
| XXX | 50 | 5 | XLVIII | 50 | 50 |
| XXXI | 500 | 50 | IL | 50 | 50 |
| XXXII | 500 | 50 | L | 50 | 50 |
| XXXIII | 5 | 50 | LI | 50 | 50 |
| XXXIV | 50 | 50 | LII | >500 | >500 |
| XXXV | 50 | 50 | LIII | >500 | >500 |
| XXXVI | 50 | 50 | LIV | >500 | >500 |
| XXXVII | 5 | 5 | LV | >500 | >500 |
| XXXVIII | 500 | 500 | LVI | 500 | 500 |
| XXXIX | 5 | 5 | LVII | >500 | >500 |
| XL | 5 | 5 | LVIII | 50 | 50 |
| XLI | 5 | 5 | LIX | 500 | 5 |
| XLII | 5 | 5 | LX | 500 | 50 |
| XLIII | 5 | 5 | LXI | >500 | >500 |
| XLIV | 50 | 50 | LXII | 5 | 50 |
| XLV | 50 | 500 | LXIII | 5 | 50 |
| XLVI | 500 | 500 | LXIV | 50 | 5 |
|  |  |  | LXV | 5 | 5 |
|  |  |  | LXVI | 5 | 5 |
|  |  |  | LXVII | 50 | 50 |

EXAMPLE 19

The efficacy of the compounds against bacteria was tested as follows:

Solutions of the compounds were prepared as in Example 18. The test organisms, in this case *Staphylococcus aureus* and *Escherichia coli*, were inoculated on nutrient agar as described in Example 12, wells were punched, and the solutions of the compounds were transferred to fill the wells. The quantity of compound in the wells amounted again to 500 μg, 50 μg and 5 μg.

After incubation at 37° for 24 hours the quantity of compound was determined at which an inhibition of the organism's growth, in the form of an inhibition zone around the corresponding well, occurred.

The concentrations at which zones of inhibition occurred for all of the compounds of this invention are reported in Table III:

TABLE III

| Compound No. | Inhibition Area at μ mg Staph. aureus | E. coli | Compound No. | Inhibition Area at μ mg Staph. aureus | E. coli |
|---|---|---|---|---|---|
| I | 500 | 500 | X | 500 | 500 |
| II | 500 | 500 | XI | 50 | >500 |
| III | 50 | 500 | XII | 50 | 500 |
| IV | 500 | >500 | XIII | 5 | 500 |
| V | 50 | 500 | XIV | 50 | 500 |
| VI | >500 | >500 | XV | 50 | 50 |
| VII | 500 | >500 | XVI | >500 | >500 |
| VIII | 50 | >500 | XVII | >500 | >500 |
| IX | 500 | 500 | XVIII | >500 | >500 |
| XIX | 500 | 500 | XLIV | 500 | 500 |
| XX | 50 | 500 | XLV | 50 | 500 |
| XXI | 5 | >500 | XLVI | 500 | >500 |
| XXII | 50 | >500 | XLVII | 5 | 500 |
| XXIII | 500 | >500 | XLVIII | 50 | 50 |
| XXIV | >500 | >500 | IL | 50 | 500 |
| XXV | 5 | 50 | L | 500 | 500 |
| XXVI | 50 | 50 | LI | 500 | 500 |
| XXVII | 50 | 500 | LII | >500 | >500 |
| XXVIII | 50 | 500 | LIII | >500 | >500 |
| XXIX | 50 | 500 | LIV | >500 | >500 |
| XXX | 50 | 500 | LV | >500 | >500 |
| XXXI | 50 | >500 | LVI | 500 | 500 |
| XXXII | 50 | >500 | LVII | >500 | 500 |
| XXXIII | 50 | 500 | LVIII | 50 | 500 |
| XXXIV | 50 | 500 | LIX | 50 | 500 |
| XXXV | 50 | 500 | LX | 500 | 500 |
| XXXVI | 500 | >500 | LXI | >500 | >500 |
| XXXVII | 5 | 500 | LXII | 5 | 50 |
| XXXVIII | 5 | 500 | LXIII | 5 | 5 |
| XXXIX | 5 | 50 | LXIV | 5 | 5 |
| XL | 5 | 5 | LXV | 500 | 500 |
| XLI | 50 | 50 | LXVI | 5 | 50 |
| XLII | 5 | 5 | LXVII | 50 | 500 |

TABLE III-continued

| Compound No. | Inhibition Area at μ mg Staph. aureus | E. coli | Compound No. | Inhibition Area at μ mg Staph. aureus | E. coli |
|---|---|---|---|---|---|
| XLIII | 5 | 5 | | | |

EXAMPLE 20

The minimum inhibitory concentration for fungi of the compounds showing an inhibition of the organism's growth at 50 μg or less in Example 18 was determined according to the following method:

A tube dilution series of the respective compound in Sabouraud nutrient broth, whose individual tubes contained concentrations of 1024 μg, 512 μg, 256 μg, 128 μg, 64 μg, 32 μg, 16 μg, 8 μg, 4 μg, 2 μg, 1.1 μg and 0.5 μg/ml, was prepared and inoculated with a photometrically standardized suspension of the test organisms or the spores thereof. After incubation at 28°C for 48 hours the lowest concentration was determined at which the organisms still failed to grow. The results are contained in the following Table IV:

EXAMPLE 21

The minimum inhibitory concentration of the compounds was determined for all compounds showing an inhibition of the bacterial growth at 50 μg or less in Example 18 according to the following method:

A tube dilution series of the respective compound in nutrient broth whose individual tubes contained concentrations of 1024 μg, 512 μg, 256 μg, 128 μg, 64 μg, 32 μg, 16 μg, 8 μg, 4 μg, 2 μg, 1.1 μg and 0.5 μg/ml was prepared and inoculated with a photometrically standardized suspension of the test organisms. After incubation, at 37°C for 48 hours the lowest concentration was determined at which the bacteria still failed to grow. The results are contained in the following Table V:

TABLE IV

| Compound No. | Minimum Inhibitory Concentration In μg/ml | | Compound No. | Minimum Inhibitory Concentration In μg/ml | |
|---|---|---|---|---|---|
| | C. albicans | A. niger | | C. albicans | A. niger |
| I | 64 | 128 | VIII | 16 | — |
| II | 1024 | 512 | IX | 16 | 128 |
| III | 32 | 64 | X | 16 | 16 |
| IV | 32 | — | XI | >1024 | — |
| V | >1024 | 64 | XII | 64 | 16 |
| VII | 32 | — | XIV | 32 | 16 |
| XV | 16 | 128 | XL | <0,5 | <0,5 |
| XIX | 16 | 32 | XLI | 2 | 1 |
| XX | 64 | 4 | XLII | <0,5 | <0,5 |
| XXI | 8 | 4 | XLIII | <0,5 | <0,5 |
| XXV | 64 | 8 | XLIV | >1024 | >1024 |
| XXVI | 8 | 4 | XLV | >1024 | — |
| XXVII | 256 | 128 | XLVII | 32 | 32 |
| XXVIII | 64 | 32 | XLVIII | 8 | 4 |
| XXIX | 8 | 16 | IL | 32 | 32 |
| XXX | 16 | 32 | LI | 256 | 256 |
| XXXI | — | 64 | LVIII | 256 | 128 |
| XXXII | — | 128 | LIX | — | 64 |
| XXXIII | 256 | 256 | LX | — | 64 |
| XXXIV | 16 | 32 | LXII | 2 | <0,5 |
| XXXV | 8 | 8 | LXIII | 32 | <0,5 |
| XXXVI | 4 | 2 | LXIV | 8 | 8 |
| XXXVII | 8 | 128 | LXV | 32 | 8 |
| XXXIX | 4 | 32 | LXVI | 4 | <0,5 |
| | | | LXVII | 128 | 128 |

TABLE V

| Compound No. | Minimum Inhibitory Concentration In μg/ml | | Compound No. | Minimum Inhibitory Concentration In μg/ml | |
|---|---|---|---|---|---|
| | Staph. aureus | E. coli | | Staph. aureus | E. coli |
| III | 512 | — | XXV | 64 | 64 |
| V | 512 | — | XXVI | 128 | 128 |
| VIII | 512 | — | XXVII | 256 | — |
| XI | >1024 | — | XXVIII | 64 | — |
| XII | 64 | — | XXIX | 128 | — |
| XIII | 32 | — | XXX | 128 | — |
| XIV | 32 | — | XXXI | 128 | — |
| XV | >1024 | >1024 | XXXII | 128 | — |
| XX | 128 | — | XXXIII | 128 | — |
| XXI | 64 | — | XXXIV | 128 | — |
| XXII | >1024 | — | XXXV | 256 | — |
| XXXVII | 16 | — | XLVIII | 128 | >1024 |
| XXXVIII | 128 | — | IL | 128 | — |
| XXXIX | 32 | >1024 | LVIII | 256 | — |
| XL | <0,5 | 32 | LIX | 1024 | — |
| XLI | 32 | 32 | LXII | 16 | 1024 |
| XLII | 32 | 32 | LXIII | 8 | 64 |
| XLIII | <0,5 | 1 | LXIV | 8 | 256 |

TABLE V-continued

| Compound No. | Minimum Inhibitory Concentration In µg/ml | | Compound No. | Minimum Inhibitory Concentration In µg/ml | |
|---|---|---|---|---|---|
| | Staph. aureus | E. coli | | Staph. aureus | E. coli |
| XLV | >1024 | — | LXVI | 32 | 128 |
| XLVII | 4 | — | LXVII | 8 | — |

EXAMPLE 22

The minimum inhibitory concentration of the compounds according to the invention in presence of serum was determined for all compounds showing an inhibition in the growth of fungi at 64 µg/ml or less in Example 20 according to the following method.

A tube dilution series of the respective compound in a Sabouraud nutrient broth was enriched by adding 10% of bovine serum. The individual tubes in the series contained the compound in concentration of 1024 µg, 512 µg, 256 µg, 128 µg, 64 µg, 32 µg, 16 µg, 8 µg, 4 µg, 2 µg, 1.1 µg and 0.5 µg/ml. Each tube was inoculated with a photometrically standardized suspension of the test organisms or spores thereof.

After incubation at 28°C for 48 hours the lowest concentration was determined at which the fungi still failed to grow. The results are contained in the following Table VI:

EXAMPLE 23

The minimum inhibitory concentration of the compounds according to the invention in presence of serum was determined for all compounds showing an inhibition of bacteria growth at 64 µg/ml or less in Example 21 according to the following method.

A tube dilution series of the respective compound in a nutrient broth was enriched by adding 10% of serum. The individual tubes in the series contained the compound in concentrations of 1024 µg, 512 µg, 256 µg, 128 µg, 64 µg, 32 µg, 16 µg, 8 µg, 4 µg, 2 µg, 1.1 µg and 0.5 µg/ml. Each tube was prepared and inoculated with a photometrically standardized suspension of the test organisms.

After incubation at 37°C for 48 hours the lowest concentration was determined at which the bacteria still failed to grow. The results are contained in the following Table VII:

TABLE VI

| Compound No. | Minimum Inhibitory Concentration In µg/ml | | Compound No. | Minimum Inhibitory Concentration In µg/ml | |
|---|---|---|---|---|---|
| | C. albicans | A. niger | | C. albicans | A. niger |
| | 64 | — | XXVIII | 256 | >1024 |
| III | 64 | 128 | XXIX | 128 | 32 |
| IV | 32 | — | XXX | 256 | 32 |
| V | — | 256 | XXI | 256 | 128 |
| VII | 32 | — | XXII | 512 | — |
| VIII | 16 | — | XXIV | 128 | 128 |
| IX | 32 | — | XXXV | 32 | 128 |
| X | 16 | 16 | XXXVI | 32 | 8 |
| XII | 256 | >1024 | XXXVII | 512 | — |
| XIII | 512 | 256 | XXXVIII | >1024 | >1024 |
| XIV | 128 | 64 | XXXIX | 64 | 128 |
| XV | 512 | — | XL | 64 | 2 |
| XIX | 16 | 32 | XLI | 128 | 8 |
| XX | 128 | 8 | XLII | 256 | 32 |
| XXI | 256 | 128 | XLIII | 128 | 64 |
| XXV | 256 | 64 | XLVII | 256 | 64 |
| XXVI | 16 | 32 | XLVIII | >1024 | 256 |
| IL | 256 | 128 | LXIII | 128 | 32 |
| L | 512 | — | LXIV | 128 | 8 |
| LIX | — | 64 | LXV | 32 | 8 |
| LX | — | 8 | LXVI | 1024 | 128 |
| LXII | 1024 | 512 | LXVII | 64 | 128 |
| | | | LXX | — | 0.25 |
| | | | LXXVI | — | 4 |
| | | | LXXVII | — | 8 |

TABLE VII

| Compound No. | Minimum Inhibitory Concentration In µg/ml | | Compound No. | Minimum Inhibitory Concentration In µg/ml | |
|---|---|---|---|---|---|
| | Staph. aureus | E. coli | | Staph. aureus | E. coli |
| XII | 1024 | — | XL | 64 | 1024 |
| XIII | 1024 | — | XLI | 128 | 512 |
| XIV | 256 | — | XLII | 256 | 1024 |
| XXI | 512 | — | XLIII | 16 | 128 |
| XXV | 256 | 512 | XLVII | 256 | >1024 |
| XXVIII | 1024 | — | LXII | 1024 | — |
| XXXVI | 256 | — | LXIII | 256 | 1024 |
| XXXVII | 1024 | — | LXIV | 1024 | — |
| XXXIX | >1024 | — | LXVI | 16 | — |

TABLE VII-continued

| Compound No. | Minimum Inhibitory Concentration In µg/ml Staph. aureus | E. coli | Compound No. | Minimum Inhibitory Concentration In µg/ml Staph. aureus | E. coli |
|---|---|---|---|---|---|
| | | | LXVII | 8 | — |

As is clearly demonstrated by the test results shown in the above tables, the compounds of this invention have the definite ability to inhibit both pathogenic bacterial and fungal growth.

We claim:

1. A compound of the formula:

wherein A is selected from the group consisting of:

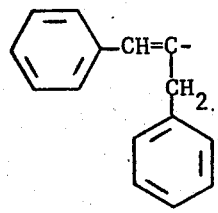

wherein B is selected from the group consisting of:

-CH₃ , and

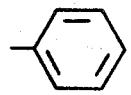

wherein D is selected from the group consisting of:

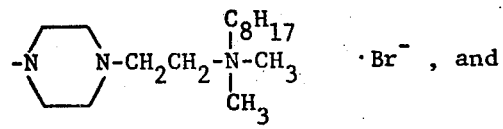

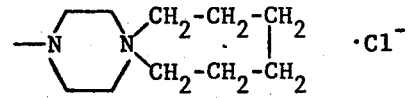

2. The compound according to claim 1 wherein A is

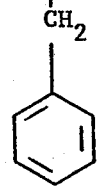

wherein B is

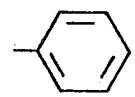

wherein D is

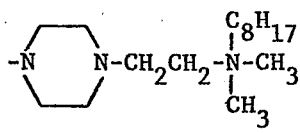

which is 2-[4-(2-benzyl-1-phenyl-3-butenyl)-1-piperazinyl]N,N-dimethyl-N-octylethanaminium bromide.

3. The compound according to claim 1 wherein A is wherein B is —CH₃, and
wherein D is
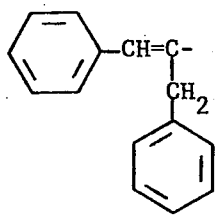
and which is 3-(2-benzyl-1-methyl-3-phenyl-2-propenyl)-3-aza-6-azoniaspiro[5.6]-dodecane chloride.
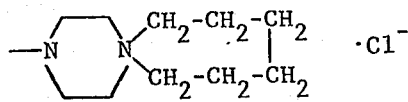
* * * * *